United States Patent [19]
Warhaftig

[11] Patent Number: 5,564,788
[45] Date of Patent: Oct. 15, 1996

[54] THORACIC LUMBAR SACRAL ORTHOSIS SUPPORT SYSTEM

[75] Inventor: Stephen Warhaftig, Scarsdale, N.Y.

[73] Assignee: Skil-Care Corp., Yonkers, N.Y.

[21] Appl. No.: 246,285

[22] Filed: May 19, 1994

[51] Int. Cl.$^6$ .................................. A47C 7/36; A61F 5/37
[52] U.S. Cl. .................. 297/464; 128/869; 297/230.12; 297/452.36; 297/483; 297/486
[58] Field of Search ........................... 297/230.1, 230.12, 297/234.3, 284.5, 452.35, 452.36, 464, 468, 483, 484; 5/465, 470, 621, 628, 633; 128/869, 870, 874, 875

[56] References Cited

U.S. PATENT DOCUMENTS

| | | | |
|---|---|---|---|
| 2,191,097 | 2/1940 | Morrison | 5/628 X |
| 2,237,057 | 4/1941 | Meyer. | |
| 2,469,268 | 9/1969 | Phillips | 128/870 X |
| 2,782,839 | 2/1957 | Cole. | |
| 3,604,750 | 9/1971 | Doering. | |
| 4,040,664 | 8/1977 | Tanaka et al. | 297/484 X |
| 4,108,492 | 8/1978 | Kirby | 5/633 X |
| 4,177,807 | 12/1979 | Ocel et al. | 297/468 X |
| 4,402,548 | 9/1983 | Mason. | |
| 4,568,125 | 2/1986 | Sckolnik. | |
| 4,655,506 | 4/1987 | Wise et al.. | |
| 4,819,278 | 4/1989 | Ramos | 297/464 X |
| 5,121,741 | 6/1992 | Bremer et al. | 128/874 X |
| 5,123,699 | 6/1992 | Warburton. | |
| 5,148,563 | 9/1992 | Klearman et al.. | |
| 5,248,182 | 9/1993 | Hittie. | |
| 5,407,248 | 4/1995 | Jay et al. | 297/464 X |

*Primary Examiner*—Peter R. Brown
*Attorney, Agent, or Firm*—Stephen A. Roen

[57] ABSTRACT

A support system for maintaining a person in a substantially upright sitting position in a wheelchair, comprises a unitary frame and a unitary cushion. The unitary frame has front and back portions, and a generally rectangularly shaped central portion having upper and lower sections. A pair of upper lateral wing frame portions extend from the upper section of the central portion, and a pair of lower lateral wing frame portions extend from the lower section of the central portion. The unitary cushion is shaped to fit over the frame and comprises, a generally rectangularly shaped central cushioned portion having upper and lower sections, a pair of upper lateral cushioned wing portions extending from the upper section of the cushioned central portion and a pair of lower lateral cushioned wing portions extending from the lower section of the cushioned central portion. The pairs of upper lateral wing frame portions and lateral cushioned wing portions, provide bracing to the left and right sides of the person's upper torso in a substantially upright position. The pairs of lower lateral frame wing portions and the upper lateral cushioned wing portions, prevent rotation of the person's pelvis. Each of the upper lateral wing frame and cushioned portions, the central frame and cushioned sections, and each of the lower lateral frame and cushioned wing portions, are generally C-shaped when viewed from the side.

16 Claims, 6 Drawing Sheets

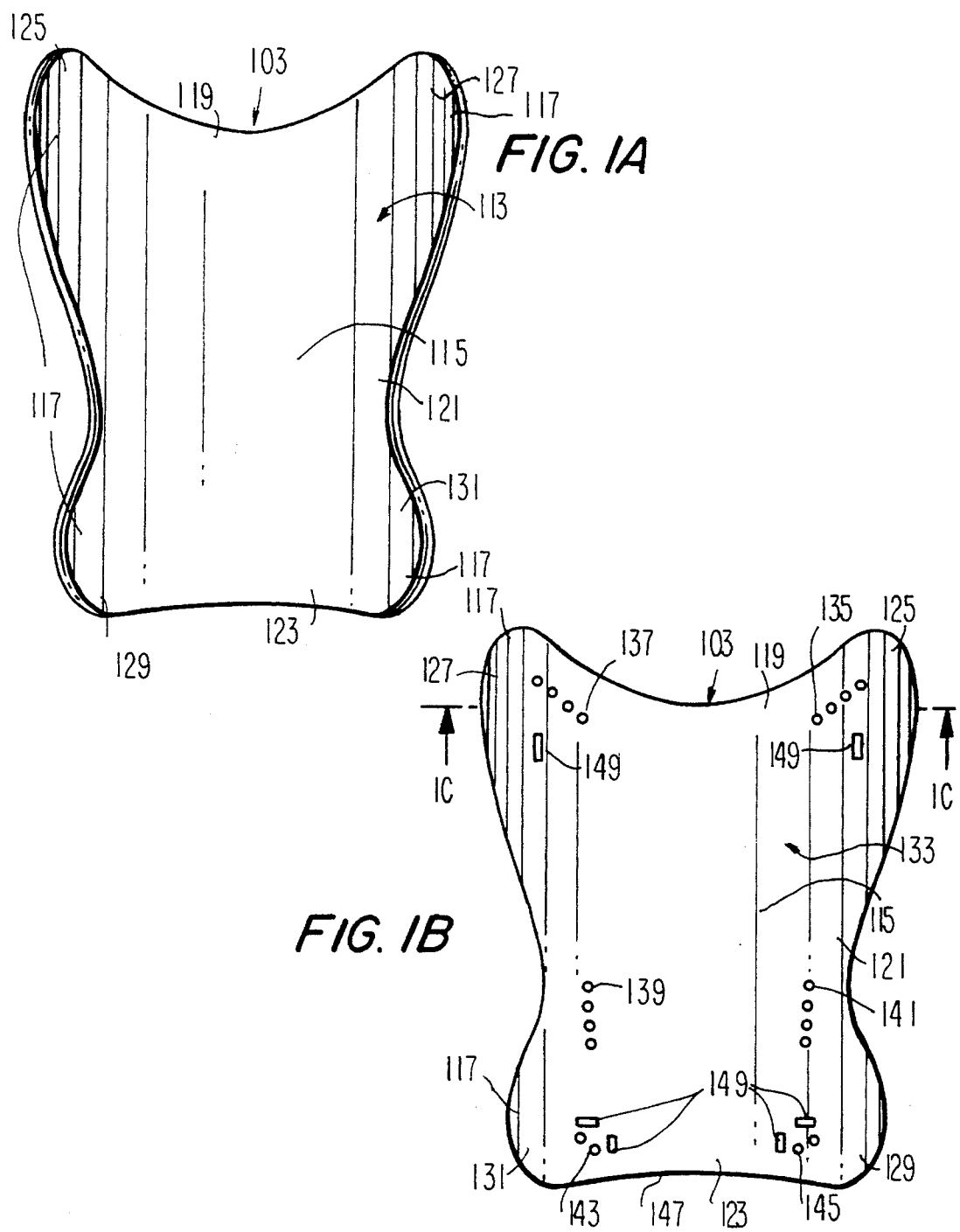
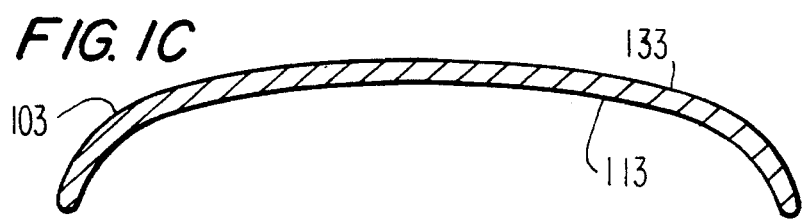

THORACIC LUMBAR SACRAL ORTHOSIS SUPPORT SYSTEM

FIELD OF INVENTION

This invention relates to a thoracic lumbar sacral orthosis support system for a person in a wheelchair. This support system maintains trunk stability by providing lateral and anterior/posterior control to the patient in a wheelchair by providing firm corrective support at the patient's shoulder and pelvic girdles.

DESCRIPTION OF THE PRIOR ART

There are numerous support systems and the like that provide support and/or restraint for a patient seated in a wheelchair.

A head and torso restraint system, is disclosed by Apter, Jr. in U.S. Pat. No. 4,541,425. It comprises an accessory for an arm chair for the use of a patient seated therein, wherein a headband secured about the patient's head is attached to a strap at the back, which is tied to the back of the chair, to limit the degree of forward moment of the patient's head. A pillow is placed adjacent each side of the patient, between each thigh of the patient and each side of the chair. Each pillow has attached thereto a strap which extends over a proximate shoulder of the patient and is tied to the back of the chair for the purpose of restraining lateral movement of the patient's torso.

A support system that can be used with wheelchairs, is disclosed by Apter in U.S. Pat. No. 5,123,699. A portable, customized patient support system is provided for maintaining a person in a substantially upright sitting position. The system has a seat cushion, a back cushion and left and right lateral trunk brace cushion. Each of the cushions is selected to conform to certain measured dimensions of the person. The cushions are secured to each other using interconnecting devices. The assembled system can be used with most conventional chairs and seats, including wheelchairs. A method of providing support for a person in a substantially upright sitting position, is also provided, which includes the steps of measuring certain dimensions of the patient, selecting appropriately sized cushions and securing the cushions together using the interconnecting devices.

An orthotic bracing system, is disclosed by Klearman et al. in U.S. Pat. No. 5,148,563. A chair restraint for supporting a patient in a sitting position in a chair or the like includes an upper torso support member having an orthotic support panel readily removable therefrom. The orthotic support panel is made from a plastic which is readily deformable by a heat gun or the like such that it may be custom fit to surround the patient both from his back and sides to provide lateral support to the patient. The upper torso restraint member includes a pair of straps extending forwardly to wrap around the front of the patient to thereby secure the patient within the upper torso restraint member. A seat cushion member includes a flat panel stiffener to provide a firm base for the patient and an interior cushioning member which is inclined generally rearwardly to thereby cradle the patient within the restraint. A center divider member of cushioning material provides two separately defined areas for receiving the patient's legs. Straps are provided for securing the upper torso restraining member to the seat cushion member, and both of those members are strapped independently to the chair frame.

A chair body support, is disclosed by Hittie in U.S. Pat. No. 5,248,182. A padded seat cushion support consists of large, vertical side cushions having extremely full and soft padding. When installed on a chair, such as a wheelchair, the cushions grip the sides of the occupant, including both sides of the occupant's head. The vertical side cushions are affixed to a central fabric panel which is fastened to the inside chair seat back by straps and also by a pocket at the rear of the panel which receives the top of the chair seat back. The vertical side cushions are slanted inward along the central panel to the top end of the panel where they are held on either side of the patient's head, thereby comfortably supporting the patient's head against unwanted lateral deflection.

SUMMARY OF THE INVENTION

A support system for maintaining a person in a substantially upright sitting position in a wheelchair, in its broadest aspect, comprises a unitary frame and a unitary cushion means. The unitary frame has front and back portions, and a generally rectangularly shaped central portion having upper and lower sections. A pair of upper lateral wing frame portions extend from the upper section of the central portion and a pair of lower lateral wing frame portions extend from the lower section of the central portion. The unitary cushion means is shaped to fit over the frame and comprises, a generally rectangularly shaped central cushioned portion having upper and lower sections, a pair of upper lateral cushioned wing portions extending from the upper section of the cushioned central portion and a pair of lower lateral cushioned wing portion extending from the lower section of the cushioned central portion. The pairs of upper lateral wing frame portions and lateral cushioned wing portions provide bracing to the left and right sides of the person's upper torso in a substantially upright position. The pairs of lower lateral frame wing portions and the upper lateral cushioned wing portions, prevent rotation of the person's pelvis. Each of the upper lateral wing frame and cushioned portions, the central frame and cushioned sections, and each of the lower lateral frame and cushioned wing portions, are generally C-shaped when viewed from the side.

An object of the present invention is to provide an improved support system for a person in a wheelchair.

Another object of the present invention is to provide an improved support for a person in a wheelchair, which support system provides improved trunk stability.

A further object of the present invention is to provide an improved support system for a person in a wheelchair and which maintains a patient in an upright posture by providing anterior-posterior-lateral rotary control and preventing trunk hyperextension.

BRIEF DESCRIPTION OF THE DRAWINGS

The above and other objects and advantages and novel features of the present invention will become apparent from the following detailed description of the preferred and alternative embodiments of the invention illustrated in the accompanying drawings in which:

FIG. 1A is a simplified front view of the preferred embodiment of the frame portion of the support system of the present invention;

FIG. 1B is a simplified rear view of the frame shown in FIG. 1A;

FIG. 1C is a simplified cross-sectional view of the frame taken along line 1C—1C shown in FIG. 1B;

DETAILED DESCRIPTION OF THE INVENTION

Figure 2A:
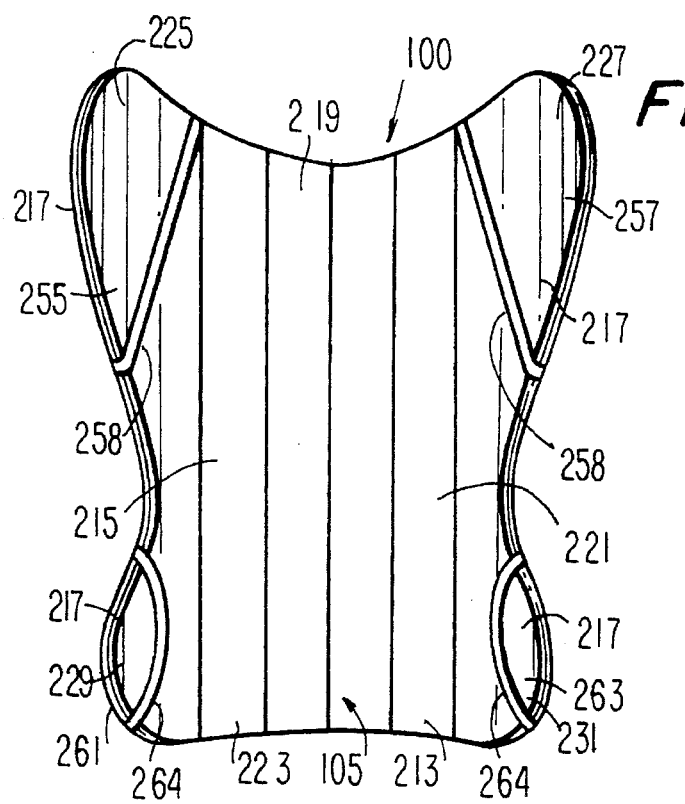
FIG. 2A is a simplified front view of the preferred embodiment of the cushion means of the support system of the present invention.

The preferred embodiment of the support system for maintaining a person or patient in a substantially upright position in a wheelchair, is generally referred to by reference numeral 100. The support system 100 is releasable affixed to a conventional wheelchair 101 (FIG. 3). Referring now to FIGS. 1A,1B,1C,2A and 2B, the support system 100 comprises a curved unitary frame 103, a unitary, vinyl covered, cushion means 105, a cushioned restraint means 107 and first and second strap means, 109 and 111, respectively. The frame 103 is preferably formed of a conventional rigid plastic. The front portion 113 (FIG. 1A) of frame 103 comprises a central, generally rectangular shaped central portion 115 and lateral portions 117. The central portion 115 comprises an upper section 119, a central section 121 and a lower section 123. Extending from the sides of the upper section 119 of the central portion 115 are a pair of upper lateral wing frame portions or shoulder wing portions 125 and 127. Extending from the sides of the lower section 123 of the central portion 115 are a pair of lower laterally extending wing frame portions or hip guide portions 129 and 131. Affixed to the back portion 133 of the frame 103 are a plurality of laterally extending conventional releasable connectors 135 and 137, each of which extends across adjacent portions of the upper lateral wing frame portions 125 and 127 and the upper section 119 of the central portion 115. Also affixed to the back portion 133 of the frame 103 are a plurality of longitudinally extending releasable connectors 139 and 141, each of which extend primarily across the central section 121 of the central portion 115. Additionally, pairs of releasable connectors 143 and 145 are affixed to the lower laterally extending wing frame portions 131 and 129, respectively; these releasable connectors 143 and 145, each extend outwardly approximately 45 degrees from the horizontal or lower edge 147 to the frame 103. Three pairs of conventional belt fastening members 149 are affixed to the back of the frame 133. A pair of these belt fastening members 149 are attached to the upper wing frame portions 125 and 127. Two pairs of the belt fastening members 149 are attached to the lower wing frame portions 129 and 131.

Figure 2B:
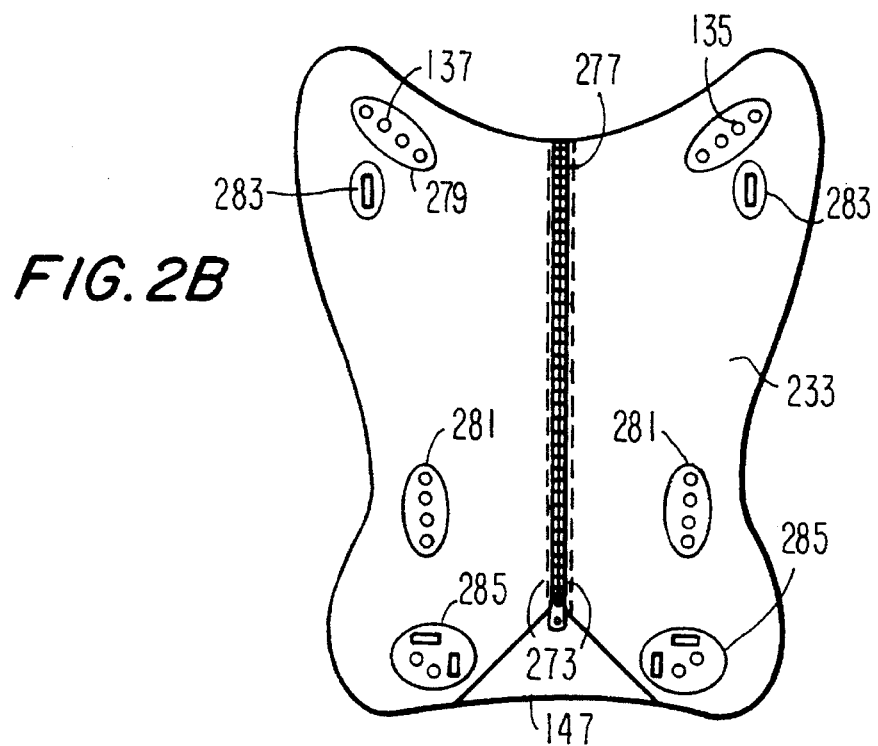
FIG. 2B is a simplified rear view of the cushion means portion shown in FIG. 2A.
Figure 3:
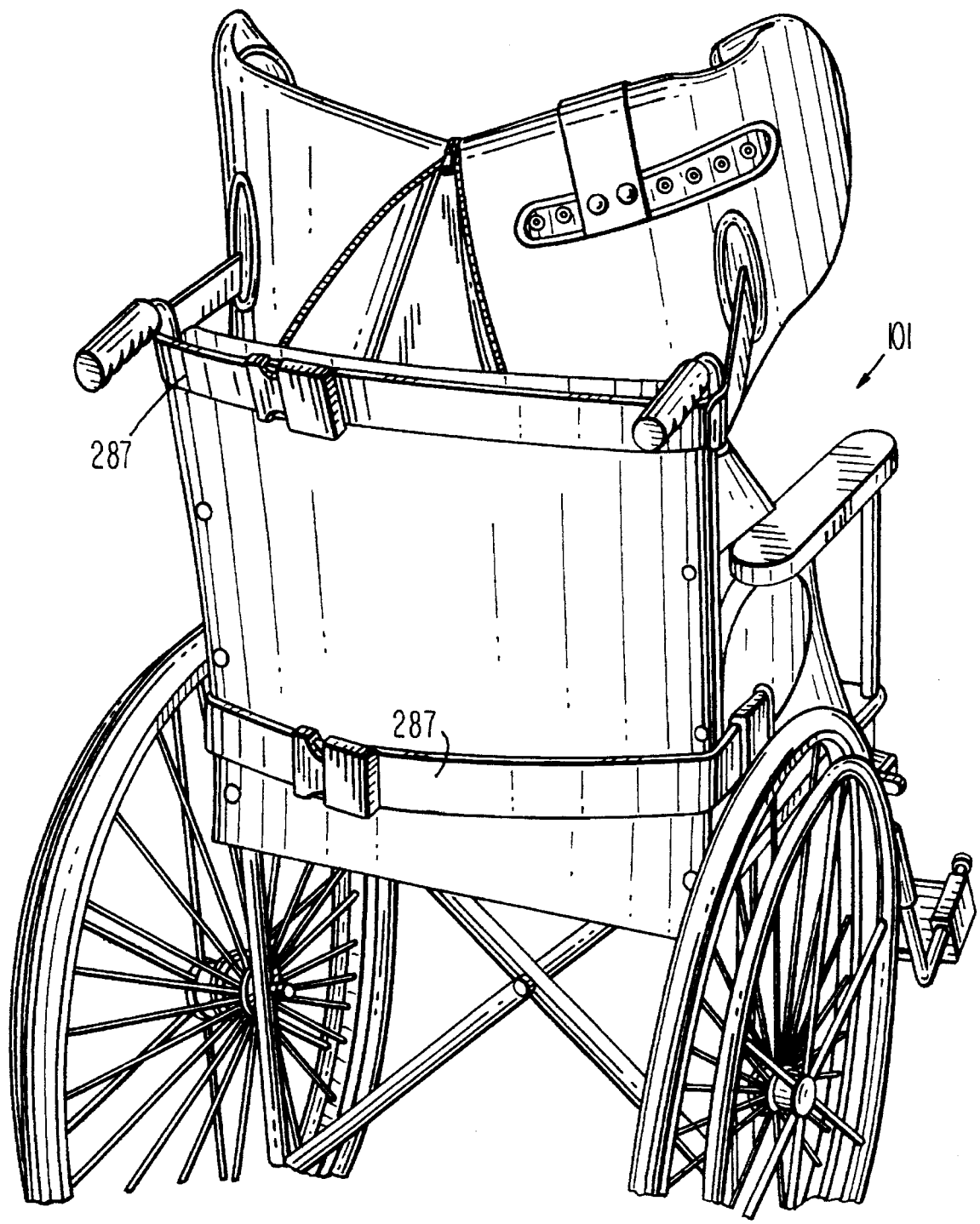
FIG. 3 is a rear view of the preferred embodiment of the support system in place in a wheelchair.
Figure 4:
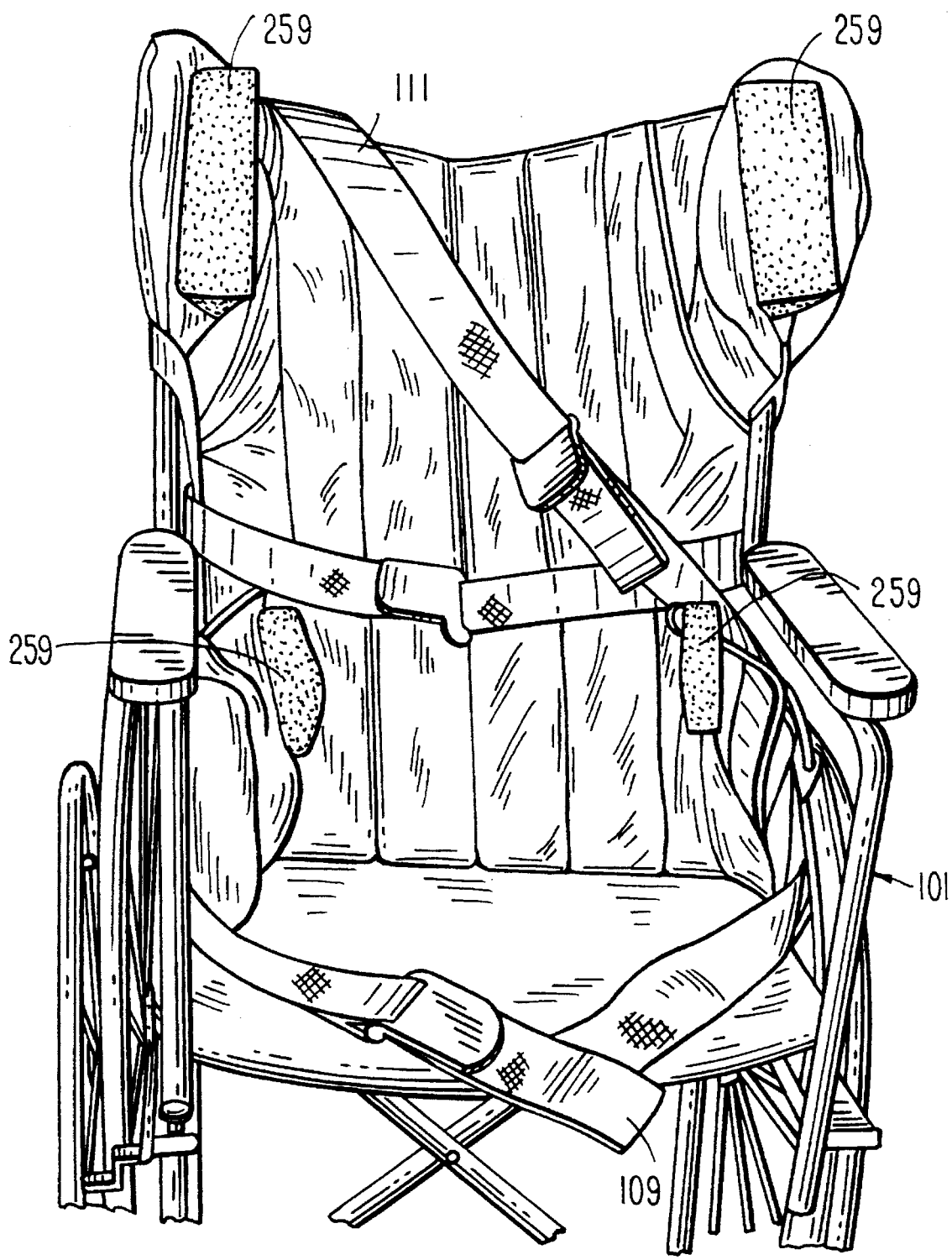
FIG. 4 is a front view of the support system of FIG. 3 in place in a wheelchair.

Referring now to FIGS. 2A and 2B, the cushion means 105 have front and back portions 213 and 233, respectively. The front portion 213 is completely cushioned and comprises a generally rectangular shaped central cushioned portion 215 and lateral cushioned portions 217. The central section 215 comprises an upper section 219, a central section 221 and a lower section 223. Extending from the sides of the upper section 219 of the central portion 215 are a pair of upper lateral cushioned wing portion means 225 and 227. Extending from the sides of the lower section 223 of the central portion 215 are a pair of lower lateral cushioned wing portion means 229 and 231. The upper lateral cushioned wing portion means 225 and 227, each comprise, at their end, a single, laterally extending, pocket 255 and 257, respectively, each of which has an inwardly extending opening 258 which is adapted to permit cushioning means 259 to be positioned therein. Such cushioning pads 259 are shown in FIG.4 and are preferably generally in the shape of a rectangular parallelpiped and are formed of conventional foam. Similarly, the lower lateral cushioned wing portion means 229 and 231, each comprise, at their ends, a single, laterally extending, pocket 261 and 263, each of which has an inwardly extending opening 264 which is adapted to permit additional, separate, cushioning means 265 to be positioned therein. The back portion 233 is affixed, at its edges, to the front portion 213, and is uncushioned and comprises two generally C-shape portions 269 and 271, joined together at its inner edges 273 and 275, respectively, by a central zipper 277. Each C-shape portion, 269 and 271, have, four cutouts formed therein, an upper longitudinal cutout 279, a centrally disposed, laterally extending, cutout 281, a narrow cutout 283, and an elliptical shaped cutout 285. Affixed to the back portion 133 of the frame 103, and disposed within the first three cutouts 279, 281 and 283 are, respectively, releasable connector 135 and 139, releasable connectors 139 and 141, and conventional belt fastening members 149. The fourth cutouts 285, each have a pair of conventional belt fasteners members 149, disposed at right angles to one another and the releasable connectors 143 and 145, discussed previously, all of which are affixed to the lower lateral wing frame portions 129 and 131 of the frame 103. The preferred releasable connectors 135, 137, 139, 141, 143 and 145 are conventional separable snap stud fastening elements.

Referring to FIG. 3, conventional, quick release adjustable straps 287, are disposed over the upper and lower portions of the back of the wheelchair 101, to attach the support system 100 to the wheelchair 101. These straps 287 are attached at their ends to the frame 103 through vertically oriented, belt fastening members 149.

Figure 5:
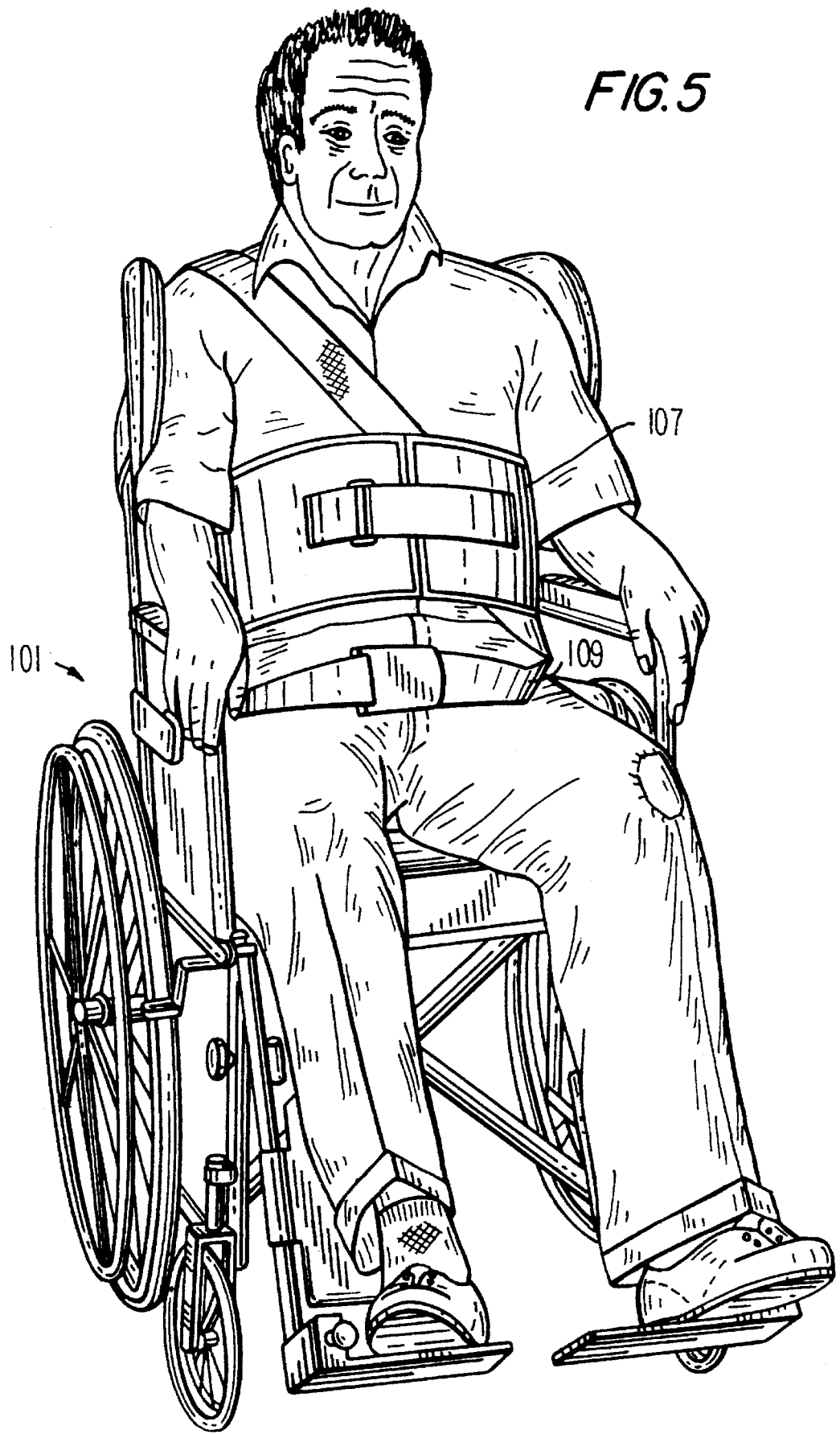
FIG. 5 a front view of the use of the preferred embodiment of the support system by a patient in a wheelchair.

Referring to FIG. 5, the cushioned restraint means or member 107 is shown drawn around the patient's lumbar region and provides lumbar support; the ends of the cushioned restraint member 107 are attached to the back 133 of the frame 103 through the releasable connectors 139 and 141. The first adjustable quick release strap or member 109 are also shown drawn around the patient's lumbar region and below the cushioned restraint member 107; the ends of the first strap 109 are attached to the back 133 of the frame 103 though the releasable connectors 143 and 145. The first strap 109, together with cushioned restraint member 107, when used as described above, prevents anterior pelvic tilt. The second adjustable strap means or member 111, when used, is drawn over the shoulder of the person seated in the wheelchair 101 and crosses over his chest; the ends of the second strap member 111 are attached to the back 133 of the frame 103 through releasable connectors 135 and the horizontally disposed belt fastening member 149. This second strap member 111 is shown right shoulder to left hip;

however it can be used left shoulder to right hip—furthermore such straps can be crisscrossed if desired. These strap(s) 111 are used to prevent forward leaning and slouching of the patient.

Figure 6A:
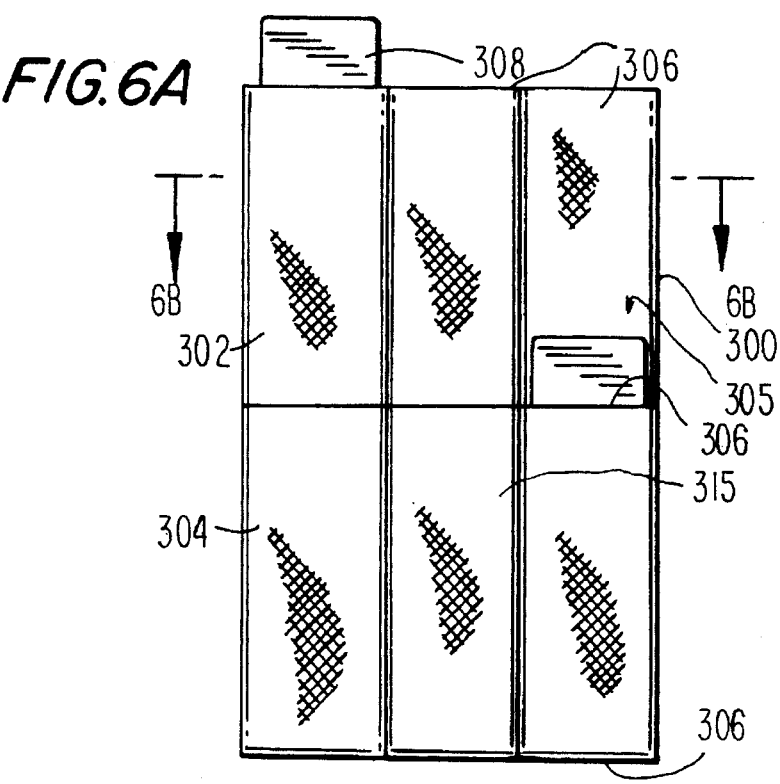
FIG. 6A is a front view of an alternative embodiment of the central portion of the cushion means of the support system of the present invention.
Figure 6B:
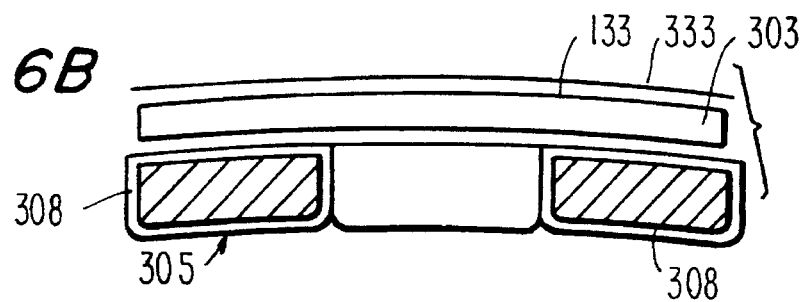
FIG. 6B is a simplified cross-sectional view of the central portion taken along line 6B—6B shown in FIG. 6A.

Referring now to FIGS. 6A and 6B, a central portion 315 of another embodiment of the support system, generally referred to by reference numeral 300, is illustrated. The cushion means 305 in this embodiment comprises first and second sets of longitudinally extending pockets, 302 and 304, respectively, disposed against the front portion 313 of the frame 303. Each pocket of the first and second sets of pockets, 302 and 304, respectively, have openings 306 at each end, and which pockets are adapted to permit removable cushioning means or pads 308 to be positioned therein. Such cushioning means 308 provide, individual, cushioned, back surfaces; various different sized pads can be utilized to provide the required alignment, including pads having different length, depths and/or different firmness. The cover of the cushion means 305 are preferable formed of vinyl, however other materials can be used, as well as utilizing resilient material of various types.

Figure 7A:
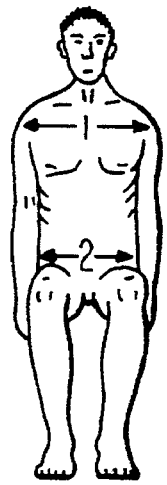
FIGS. 7A and B illustrate the dimensions of a patient which are measured before an appropriate support system is manufactured.
Figure 7B:
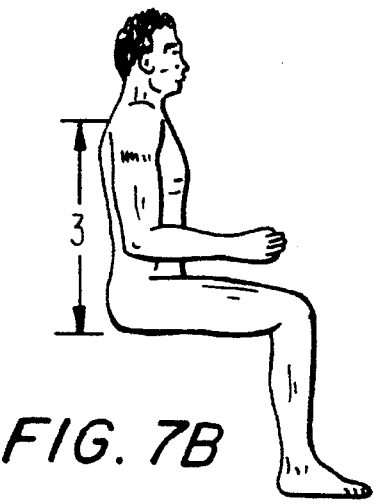

Each support system can be made to conform to the specific requirements of individual patients. To custom fit such support system, various measurements, as shown in FIGS. 7A and B, are required. Such measurement required are shoulder width 1, pelvic girdle width 2, and height from a seating surface to the top of shoulder 3.

Minor adjustment of the shoulder wing portions 125 and 127 and/or hip girdle portions 129 and 131 of the frame 103 can be accomplished by the application of a conventional heat gun.

In summary, the modular support system maintains trunk stability by providing lateral and anterior/posterior control. This is achieved by a unitary system which provides corretive support at the seated patient's shoulder and pelvic girdles. The system is uniquely designed for patients with spinal deformaties, and is particularly useful for patients with contractures of one or both upper extremities; it is also very effective for patients who are unable to tolerate lateral support under the axilla.

More particularly the shoulder wing portions 125 and 127 offer firm support to prevent lateral leaning and additional support is easily provided by the use of additional cushioning pads 259. The adjustable chest strap 111 provides anterior trunk support, that is, prevents forward leaning and slouching. The hip guide portions 129 and 131 provide pelvic rotation control, that is, the hip guide portions prevent rotation and assist in the maintenance of symmetrical weight bearing. The cushioned restraint means 107 provides lumbar support and prevents anterior pelvic tilt when used in conjunction with the pelvic or first strap 109. Since the pelvic strap 109 is angled at 45 degrees, sliding is prevented by eliminating posterior pelvic tilt. The use of a rigid frame 103 insures firm support of the shoulder and pelvic girdles, and provides posterior control to prevent hyperextension of the trunk. The rows of lateral and longitudinal snap studs 135, 137, 139, 141 and 143 are utilized for the chest, pelvic and lumbar support straps, 111, 109 and 107, respectively. These releaseable connectors permit the needed range of adjustment for optimal strap and support positioning to accommodate the patient's particular height, weight and girth. Since the cushion means 105 is easily removed from the frame 103, it is easily cleaned. Providing pockets 258 and 264 in the shoulder wing portions and hip guide portions, respectively, permit on-site placement of additional cushioning or foam padding 259 for patient's who require increased control of these areas. Minor on-site adjustments of the shoulder wing portions and hip guide potions of the plastic frame 103 can be done with a heat gun.

Although the present invention has been described in conjunction with a preferred embodiment and single alternative embodiment, it is to be understood that modifications and variations may be resorted to without departing from the spirit and scope of the invention, as those skilled in the art will readily understand. Such modifications and variations are considered to be within the purview and scope of the invention and the appended claims.

What is claimed is:

1. A support system for maintaining a person in a substantially upright sitting position in a wheelchair, comprising:

a unitary frame having front and back portions, comprising, a generally rectangularly shaped central portion having upper and lower sections, a pair of upper lateral wing frame portions extending from the upper section of said central portion, a pair of lower lateral wing frame portions extending from the lower section of said central portions, and a unitary cushion means being shaped to fit over the frame, comprising:

a generally rectangular shaped central cushioned portion means having upper and lower sections, a pair of upper lateral cushioned wing portions means extending from the upper section of said cushioned central portion, a pair of lower lateral cushioned wing portion means extending from the lower section of said cushioned central portion, said pairs of upper lateral wing frame portions and lateral, cushioned wing portions means extending forwardly substantially as far as said pairs of lower lateral wing frame portions and lower lateral cushioned wing portion means, for bracing the left and right sides of the person's upper torso in a substantially upright position and for providing firm support of the person's shoulder girdle, said pairs of lower lateral frame wing portions and lateral cushioned wing portions means, for preventing rotation of person's pelvis and for providing firm support of the person's pelvic girdle, said unitary means being generally C-shaped when viewed from the side, and each of said upper lateral wing frame portions and cushioned wing portion means and each of said lower lateral wing frame portions and cushioned wing portion means extending essentially transverse from said central portion.

2. A support system as recited in claim 1, wherein said frame further comprises a plurality of laterally extending releasable connectors affixed to the back portion of the frame and extending across adjacent portions of the upper lateral wing frame portions and the upper sections of the central portion of the frame.

3. A support system as recited in claim 2, wherein said frame further comprises a plurality of longitudinally extending releasable connectors affixed to the back portion of the frame and extending primarily across the central section of the central portion of the back portion of the frame.

4. A support system as recited in claim 4, wherein said frame further comprises a plurality of longitudinally extending releasable connectors affixed to the back portion of the frame and extending primarily across the central section of the central portion of the back portion of the frame.

5. A support as recited in claim 2, further including second strap means releasably attached to at least one of said plurality of laterally extending releasable connectors, adapted to be drawn over the shoulder of a person seating in said wheelchair and crossed over the chest of said person.

6. A support system as recited in claim 1, wherein each of said upper and lower lateral, cushioned, wing portion means comprises a generally laterally extending open pocket having an opening which is adapted to permit additional, separate, cushioning means to be positioned within said open pocket.

7. A support system as recited in claim 3, wherein the opening of each said pockets being inwardly extending and which is adapted to permit additional cushioning means to be positioned therein.

8. A support system as recited in claim 7, wherein said additional cushioning means being position therein while said central cushioned portion is connected to said lateral cushioned wing portion means.

9. A support system as recited in claim 6, wherein said additional cushioning means being positioned therein while said central cushioned portion is connected to said lateral cushioned wing portion means.

10. A support system as recited in claim 1, further including cushioned restraint means connected to said central portion of said frame and adapted to be drawn around the patient's lower torso region for providing lumbar support to said person.

11. A support system as recited in claim 10, further including a plurality of longitudinally extending releasable connectors and first strap means releasably attached to at least one of said plurality of longitudinally extending releasable connectors affixed to the back portion of said frame and adapted to be drawn over the person's lumbar region, whereby said first strap means and said cushion restraint means, when drawn over said patient's lumbar region prevents anterior pelvic tilt.

12. A support system as recited in claim 6, further comprises a plurality of longitudinally extending releasable connectors affixed to the back portion of the frame and extending primarily across the central section of the central portion of the back portion of the frame.

13. A support system as recited in claim 1, wherein said cushioned means comprises a plurality of separate longitudinally extending pockets, each said pocket having at least one opening, disposed against the front portion of said frame and adapted to permit additional cushioning means to be positioned therein.

14. A support system as recited in claim 10, further comprising a plurality of longitudinally extending pockets.

15. A support system as recited in claim 10, wherein said plurality of longitudinally extending pockets comprises, first and second sets of longitudinally extending pockets disposed, respectively, against the front portion of said frame.

16. A support system for maintaining a person in a substantially upright sitting position in a wheelchair, comprising:

a unitary frame having front and back portions, comprising, a generally rectangularly shaped central portion means having upper and lower sections, comprising, a pair of upper lateral wing frame portions extending substantially transversely from the upper section of said central portion, a pair of lower lateral wing frame portions extending substantially transversely from the lower section of said central portions, and a unitary cushion means being shaped to fit over the frame, comprising, a generally rectangularly shaped central cushioned portion having upper and lower sections, a pair of upper lateral cushioned wing portion means extending from the upper section of said cushioned central portion, a pair of lower lateral cushioned wing portion means extending from the lower section of said cushioned central portion, each of said upper and lower lateral, cushioned wing portion means comprising a generally laterally extending pocket means adapted to permit additional, separate, cushioned means to be positioned therein, said pairs of upper lateral swing frame portions and lateral cushioned wing portion means extending forwardly substantially as far as said pairs of lower lateral wing frame portions and lower lateral cushioned wing portion means, for bracing the left and right sides of the person's upper torso in a substantially upright sitting position, said pairs of lower lateral frame wing portions and upper lateral cushioned wing portion means, for preventing rotation of a person's pelvis, said unitary means being generally C-shaped when viewed from the side, a plurality of laterally extending releasable connectors affixed to the back portion of the frame and extending across adjacent portions of the upper lateral wing frame portions and the upper sections of the central portion of the frame, a plurality of longitudinally extending releasable connectors affixed to the back portion of the frame and extending primarily across the central section of the central portion of the back portion of the frame, cushioned restraint means connected to said central portion of said frame adapted to be drawn around the patient's lower torso region for providing lumbar support to said person, first strap means releasably attached to at least one of said plurality of longitudinally extending releasable connectors affixed to the back portion of said frame and adapted to be drawn over the person's lumbar region, whereby the said first strap means and said cushioned restraint, when drawn over said patient's lumbar region prevents anterior pelvic tilt, and second strap means releaseably attached to at least one of said plurality of laterally extending releasable connectors, adapted to be drawn over the shoulder of a person seated in said wheelchair and crossed over the chest of said person.

\* \* \* \* \*